United States Patent [19]

Girouard

[11] Patent Number: 4,682,979
[45] Date of Patent: Jul. 28, 1987

[54] COLON WASHING METHODS AND APPARATUS

[76] Inventor: Jimmy J. Girouard, P.O. Box 1401, Groves, Tex. 77619

[21] Appl. No.: 744,958

[22] Filed: Jun. 17, 1985

[51] Int. Cl.⁴ .............................................. A61M 31/00
[52] U.S. Cl. ..................................... 604/48; 604/113; 604/118; 604/131; 604/151; 604/259; 128/DIG. 12; 222/266; 222/331
[58] Field of Search ..................... 604/48, 54, 80, 82, 604/83, 113, 114, 118, 131, 151, 257, 259; 128/DIG. 12; 222/266, 331

[56] References Cited

U.S. PATENT DOCUMENTS

| | | | |
|---|---|---|---|
| 1,383,708 | 7/1921 | Farr | 222/331 |
| 1,949,575 | 3/1934 | Miller | 604/80 |
| 2,022,742 | 12/1935 | Salerni | 604/118 |
| 2,131,516 | 9/1938 | Leffert et al. | 604/54 |
| 2,420,586 | 5/1947 | Welles | 604/83 |
| 2,617,416 | 11/1952 | Condit | 604/259 |
| 3,044,465 | 7/1962 | Anderson et al. | 604/114 |
| 3,626,941 | 12/1971 | Webb | 604/114 |
| 4,190,059 | 2/1980 | Holt | 604/259 |
| 4,309,995 | 1/1982 | Sacco | 604/259 |
| 4,321,920 | 3/1982 | Gillig | 604/54 |

Primary Examiner—C. Fred Rosenbaum
Assistant Examiner—Mark Rooney
Attorney, Agent, or Firm—Nies, Webner, Kurz & Bergert

[57] ABSTRACT

Colon washing apparatus and methods wherein water flow to the colon may be by gravity flow or by pumped flow, wherein temperature control of the wash water is controlled by mixing of hot and cold water or by means of a water heater means, wherein wash water pressure is controlled by water head or by pump output pressure, and by pressure flow valve controls, wherein pulsating water flow may be used, wherein oxygen may be introduced into the wash water, wherein water penetration into the colon may be assisted by abdominal massage, wherein the nozzle may be introduced through the colon by water jet action, and wherein angular water jets from the nozzle may cause washing action ahead of the nozzle. The apparatus is fail-safe in that alternative modes of operation are available in case of power failure. The patient can control the apparatus in case of operator absence or patient discomfort.

10 Claims, 8 Drawing Figures

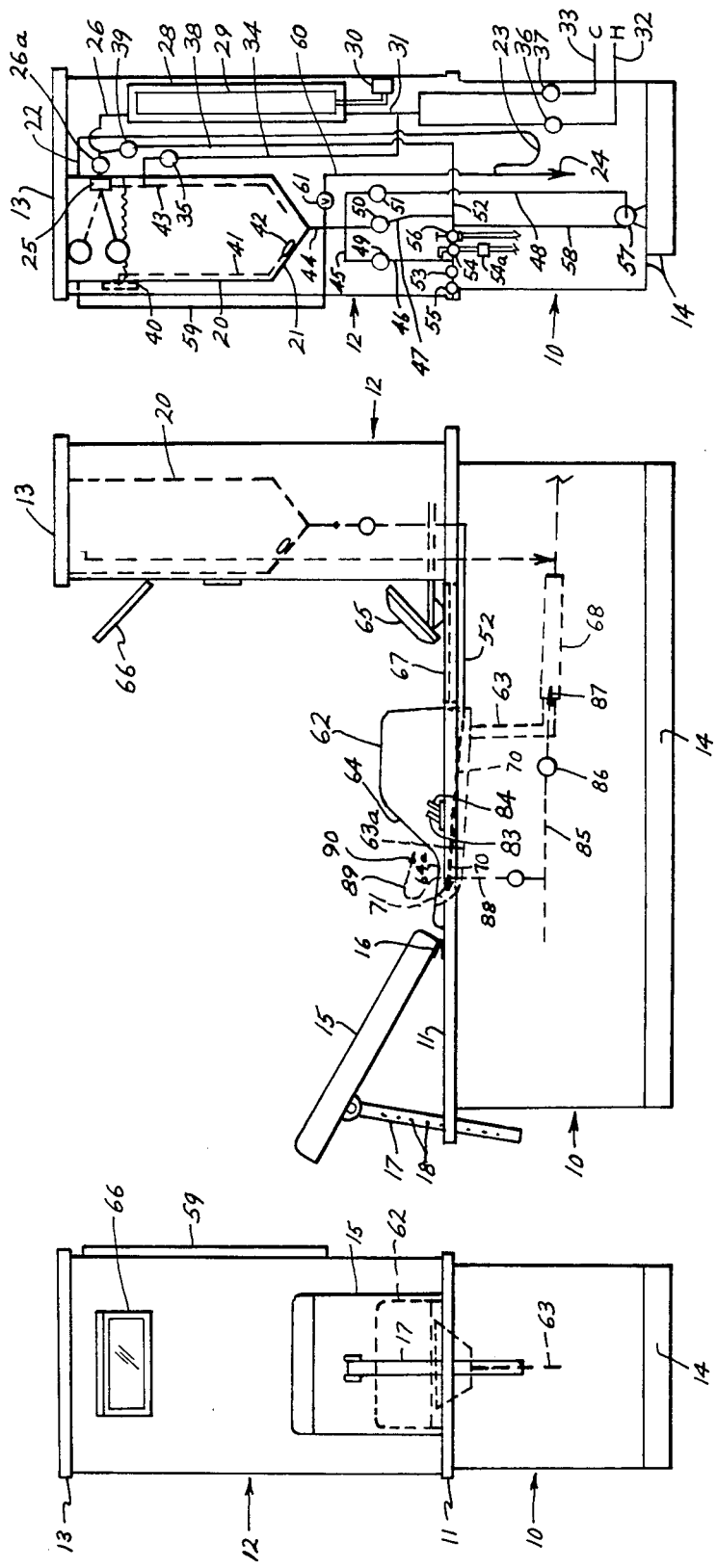

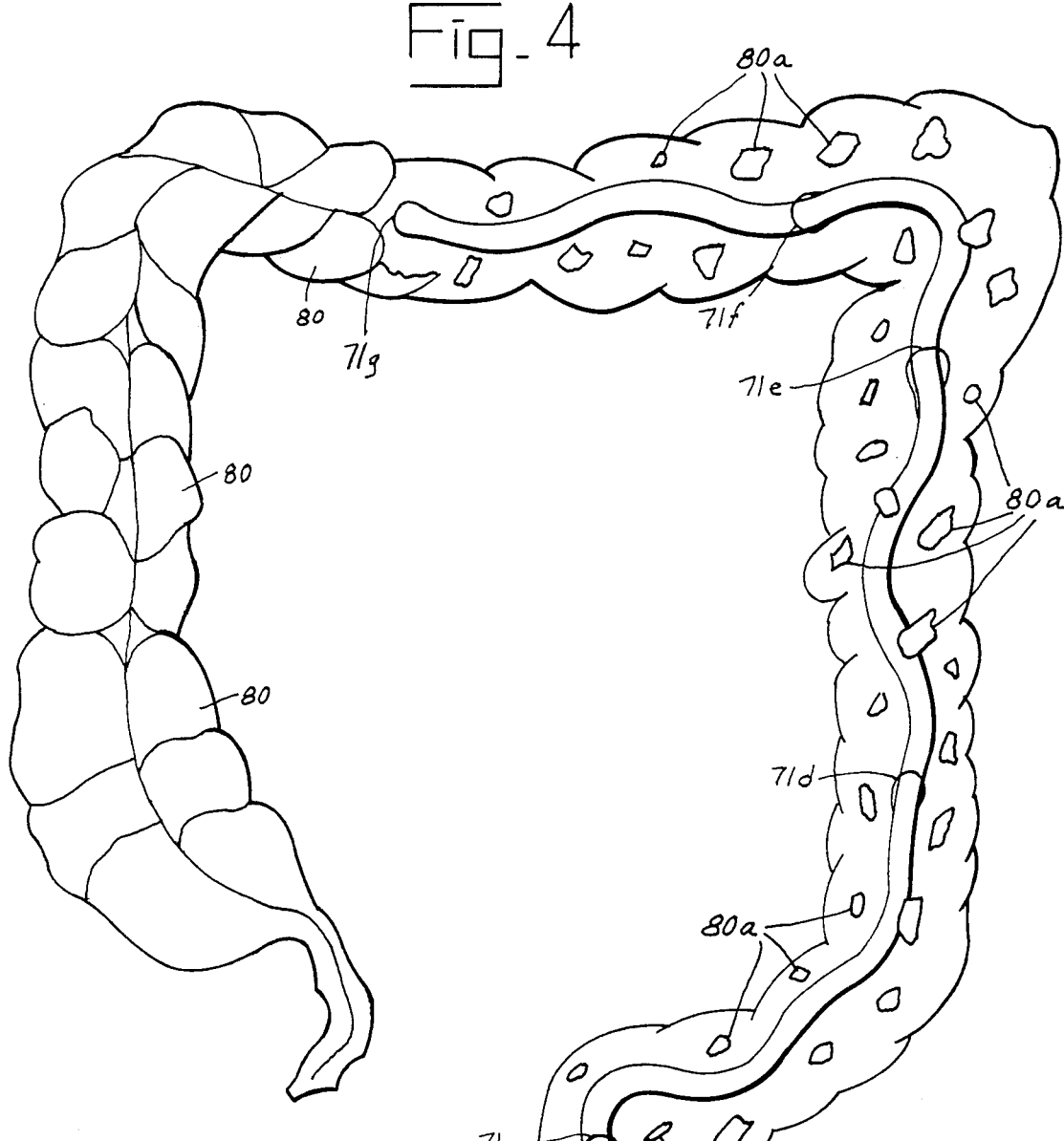
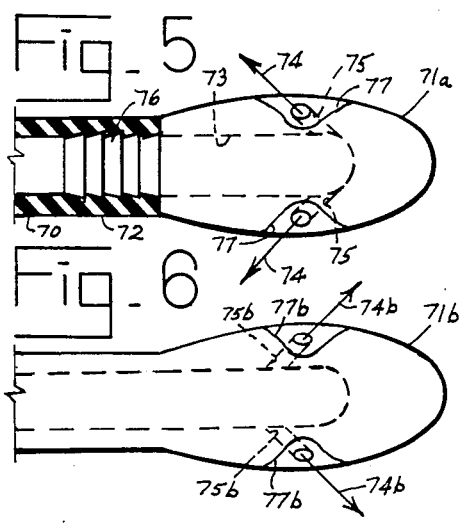

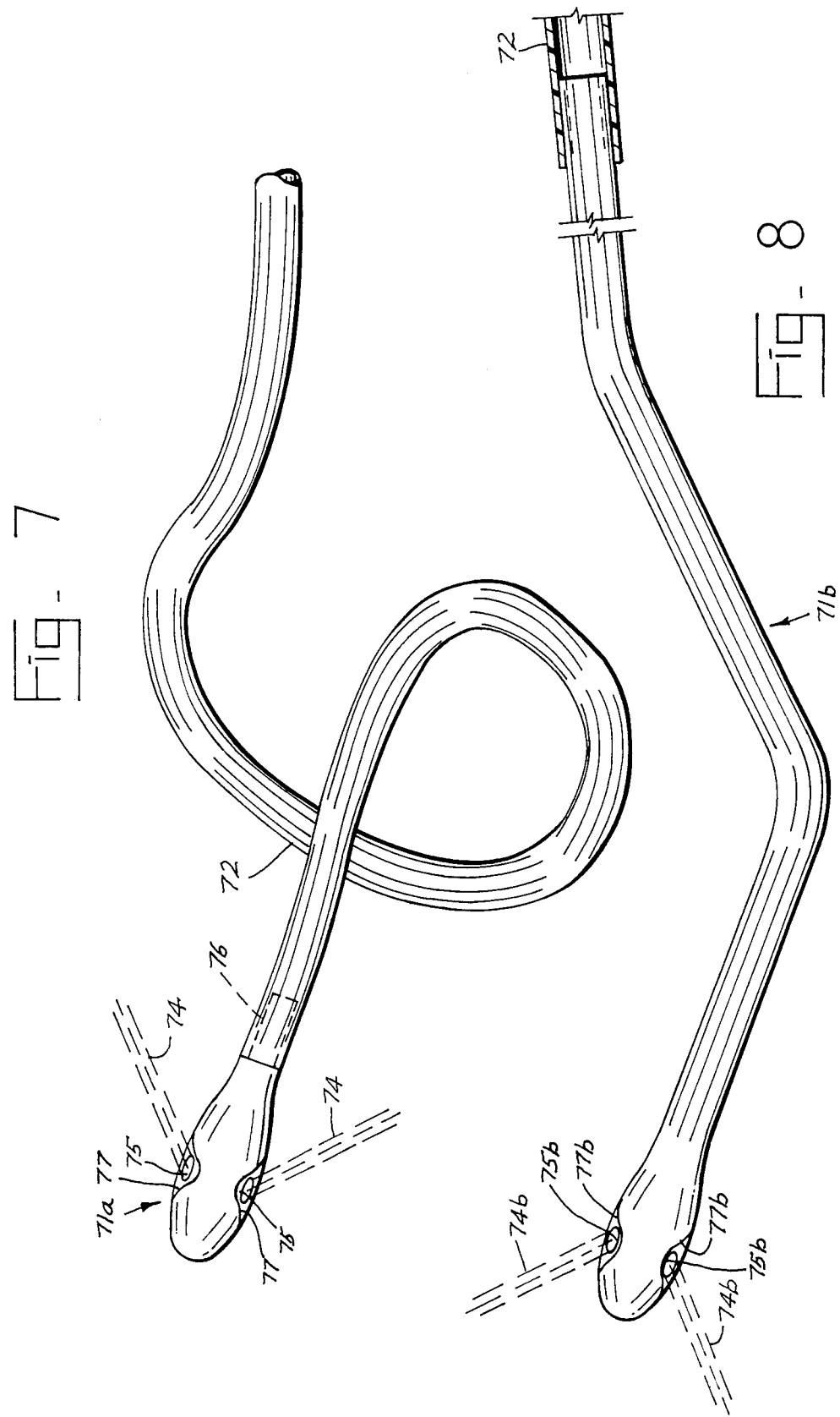

COLON WASHING METHODS AND APPARATUS

BACKGROUND OF THE DISCLOSURE

In persons having normal bowel activity, the large intestine, or colon, may retain a large amount of matter which accumulates and does not move out of the colon during long periods of time. In persons having bowel dificiencies, the matter in the colon may be considerably less mobile, and impacted feces may remain in place in the colon for very extended periods of time. Such conditions of more or less permanent residence of feces material in the colon may lead to toxic effects, inflamation of the lining of the colon, or other serious complications. Therefore, cleaning of the colon to avoid these difficulties is desirable. Touchberry U.S. Pat. No. 2,564,135 teaches a colonic therapy table device for the same general purpose, but does not provide flow and pressure controls and temperature controls such as are present in the apparatus herein disclosed, and does not provide the operating options which are afforded by the apparatus disclosed herein. The apparatus disclosed in U.S. Pat. No. 3,004,537, designed for mounting within a bathtub, also does not have adequate pressure, temperature, and flow controls to adequately protect the patient, and is not mobile as is the herein disclosed apparatus to be adaptable for taking from place to place for use. Touchberry U.S. Pat. No. 3,401,694 shows an apparatus having temperature and pressure controls for maintaining constant temperature and pressure of water used for colonic irrigation, but does not show any means for controlling washing of material from the colon such as the present invention presents.

Waysilk U.S. Pat. No. 3,771,522 shows a mixing head type of nozzle through which mixtures of water and medication can be injected into the colon. The water is maintained at low pressure and is gravity fed. No backup operation is provided. U.S. Pat. No. 4,187,057 to Xanthopoulos discloses an infusion pump having provision for gravity flow, and has numerous operation indicators. U.S. Pat. No. 4,256,437 to Brown shows another infusion pump apparatus. Fisher U.S. Pat. No. 1,847,954 shows a colon irrigation system having a check valve to prevent contamination of the water feed system. Hudson U.S. Pat. No. Re. 28,130 discloses a gravity fed irrigation system capable of use for enemas, vaginal infusion, and other related treatments, the unit being self contained. Ryan et al U.S. Pat. No. 1,945,031 discloses a lavage table having patient support assemblies, but having no water pressure and temperature controls, and no alternative procedures for use in event of equipment failure. U.S. Pat. No. 2,027,588 to Hannon discloses an assembly for mixing liquid treatment agents and for urging them into the patient by air pressure. No temperature or pressure controls are shown. Touchberry U.S. Pat. No. 2,506,183 teaches an apparatus designed for comfortable support of the patient, but does not disclose any specific apparatus for controlling temperature and pressure of the treating liquid.

SUMMARY OF THE INVENTION

This invention presents apparatus for use in irrigating and washing the colon of a living person, the apparatus providing primary and secondary means for controlling water flow, pressure and temperature. Water may be supplied by gravity from an elevated tank, or may be supplied directly from water supply lines. Temperature may be controlled by one or more thermostats in the elevated tank, or by flow controls from hot and cold water sources. Water flow may be controlled by valves or by pressure regulation devices. The apparatus includes an inclined position patient support which is adjustable. A safety switch operable by the patient is provided. A sight glass is provided for observation of liquids and solids drained from the colon, and which through a mirror can be observed by the patient. All controls are within easy reach of the operator. Water injection nozzles are provided which in one form is self-propelled into the colon. Many other features are incorporated in the apparatus, which has as primary goals patient comfort and safety, and ease of operation.

A principal object of the invention is to provide colon irrigation and washing apparatus which is safe and convenient and which is easily operated. Another object of the invention is to provide such apparatus which is mobile and which can be used without provision of special plumbing facilities. A further object of the invention is to provide such apparatus which has standby or backup assemblies so that the apparatus may be used under almost any conditions. Another object of the invention is to provide such apparatus which is self contained and thereby easily moved as a unit. Yet another object of the invention is to provide such apparatus which is reliable and dependable in use.

Other objects and advantages of the invention will appear from the following detailed descriptions of preferred embodiments, reference being made to the accompanying drawings.

BRIEF DESCRIPTIONS OF THE DRAWINGS

FIGS. 1-3 are partly schematic drawings showing a preferred form of apparatus according to the invention.

FIG. 4 is a schematic drawing showing a method of use of the apparatus according to the invention.

FIGS. 5-6 are elevations showing two forms of nozzles which may be used in connection with the invention.

FIG. 7 is a plan view showing a nozzle as shown in FIG. 5 connected to a flexible conduit.

FIG. 8 is a side elevation of the nozzle shown in FIG. 6 in complete form.

DESCRIPTION OF THE PREFERRED EMBODIMENTS

Referring now to the drawings in detail, and first to FIGS. 1-3, a cabinet 10 having a flat overhanging top 11 supports a second upstanding cabinet 12 which also has an overhanging top 13. Both cabinets may have doors or openings (not shown) to permit storage therein and to permit access into their interiors. Cabinet 10 has a lower edge recess 14 to accomodate the feet of a person standing in front of the cabinet. The access into cabinet 12 is preferably from the side shown as the right side in FIG. 1, and shown frontally in FIG. 2. A cushioned slab-shaped back support 15 is hinged at its edge 16 (hinge not shown) across the top of top 11, and is elevated at its left end by an adjustable prop bar 17 which has plural perforations 18 to permit multi-level positions of a cross pin above an opening through top 11 through which bar 17 extends. Any other suitable form of adjustment for the elevation of the left end support 15 may be substituted.

Cabinet 12 has supported therein a water tank 20, tank 20 having a conical bottom 21. A drain conduit 22 extends from the upper end portion of tank 20 to a P-trap 23 connected to a drain 24 leading to a sewer. A float controlled valve 25 controls the extent of filling of tank 20 from the water supply conduit 26. Conduit 26 leads from a tank 28 within which is a heater coil 29 energized by electrical temperature controller 30 connected to a suitable source of electric power, not shown. Water is fed into tank 28 from conduit 31 which leads from hot and cold water sources H and C through conduits 32, 33, respectively. Conduit 34 and valve 35 provide an alternate route for introduction of water into tank 20. As will be readily understood, water passing through tank 28 may be heated by operation of coil 29. Water in tank 20 may be heated by circulating water from tank 20 through tank 28. The temperature of water entering tank 28, and passing through it to tank 20, may be controlled by adjustment of the flows from H and C by means of valves 36, 37 in conduits 32, 33, and/or temperature controller 30. Water leaving tank 28 may be diverted through conduit 38 by opening valve 39. Tank 20 supports a temperature indicator 40 which includes a capillary tube 41 and bulb 42 immersed in the water in tank 20. Conduit 43 conducts the water entering tank 20 from float controlled valve 25 to the bottom of tank 20. In case of overfilling of tank 20, the excess water overflows from tank 20 through conduit 22.

Water drained from tank 20 passes through conduit 44 to manifold including conduit 45 and branch conduits 46, 47, 48 controlled by valves 49, 50, 51, respectively. Conduit 46 leads to cross conduit 52 between a check valve 53 and a solenoid valve 54 in conduit 52. Conduit 52 also has an oxygen injection valve 55 and a pressure flow control valve 56 in the positions shown in the drawing.

A pump 57 located in the bottom of cabinet 10 receives water flow from conduit 48 and pumps the water through conduit 58 to cross conduit 52. Cross conduit 52 is connected to conduit 38 previously described so that pump 57 can be used to circulate water through tank 20, in which case valves 36, 37 should be closed. Conduit 47 leads from manifold conduit 45 to cross conduit 52, so that water may be drained by gravity from tank 20 into the cross conduit. A sight tube 59 connected at its upper end to an upper level of tank 20 and at its lower end to conduit 44, as shown, enables determination of the water level in tank 20. A conduit 60 connected from conduit 44 to drain 24, and including a valve 61 enables draining of tank 20.

The primary route for delivering water to the patient is through valve 50 (with valves 49, 51, and 39 closed) into cross conduit 52, through control valve 56, solenoid valve 54, check valve 53, and to the patient. Using this route the pressure is controlled by the pressure-flow control valve 56 but can never exceed pressure delivered by actual height of the water column of a full tank 20.

Alternate routes, in order of preference, are as follows:

(a) Flowing water from a full tank 20, through valve 51 to pump 57, discharging pump water into manifold 52, with valves 39, 49, and 50 closed. This route and the pump are used when slightly more pressure is desired. To increase the pressure to the patient the pressure-flow control valve 56 may be adjusted to allow slightly more pressure and flow to achieve the desired results of removing impacted matter in the colon that will not break loose.

(b) Another route can be used with valve 26a closed in conduit 26, with valves 49, 50, and 51 closed. Valve 39 in conduit 38 is opened and temperature controlled water from hot water heater 28 at city pressure is controlled and reduced in cross conduit 52 by pressure-flow control valve 56. This route can be used when the float valve 25 is out of order, or when more pressure is desired than the pump can deliver.

(c) Another route can be used with valves 39, 50, and 51 closed and with manual valve 49 open, by-passing the electric solenoid valve 54 should there be a power failure. This condition would allow flow to the patient, by gravity, of a specific pressure as dictated by the height of the tank 20 and its overflow 22.

Procedure (c) is the only operating condition under which the temperature of the water passing through the hot water heater 28 into tank 20 will be controlled by adjustment of valves 36 and 37.

Top 11 of cabinet 10 has an opening therethrough, not shown, around which a molded support 62 is fixed. Support 62 is shaped to received and support the buttocks of a person whose back is supported by back support 15, the rectum of the person thereby being supported above a drain through support 62. The rectum is supported above the drain 63 and over an inclined drain surface 63a of support 62 which slopes downwardly toward the drain. Inclined surfaces 64 at the exterior of 62 prevent the buttocks of the person from sliding downward beyond their proper position above the inclined surface 63a. The buttocks rest on console seat surfaces 64a. The thighs of the person to be treated angle upwardly from surfaces 64, the knees being elevated, and the lower legs extending angularly downwardly from the knees so that the feet are supported on inclined foot supports 65. Two foot supports 65 are provided, one at each side of the table top 11, and each being carried at the end of a bar slidably disposed through the lower end of cabinet 12 so that their positions can be adjusted to match the extent of the legs of the person. A person lying in the position described may, by looking at the inclined mirror supported on cabinet 12, see the top of table 11, the mirror angle being adjustable for this purpose. The mirror is indicated by reference numeral 66. A transparent sheet of glass 67 is disposed over an opening in top 11 to give a view of the interior of cabinet 10. A transparent drain tube 68 connected into drain 63 allows viewing of materials passing through the drain tube. The patient, by way of mirror 66, and the operator of the apparatus, may thus look at the materials in tube 68. Past tube 68, drain 63 is an opaque conduit which may be connected to a sewer or toilet or other facility for disposal of the drained matter. Drain 63 and drain 24 may be combined, and a trap may be incorporated with drain 63 to restrain odors and noxious gasses from passing upward through the drain.

A flexible tube 70, FIG. 1, is connected to the end of cross conduit 52, which extends through an appropriate opening into the interior of support 62, tube 70 being as long as desired depending on the type of treatment to be given to the patient. A nozzle 71 is carried at the end 72 of tube 70. For some treatments, the nozzle is inserted only a short distance into the bowel of the patient, and for other treatments the nozzle may travel or propel its way a considerable distance into the bowel.

Referring now to FIGS. 5 and 6 of the drawings, the nozzle 71 may take either of the forms 71a (FIG. 5) or 71b (FIG. 6). Nozzle 71a has a central passage 73 which terminates short of the forward end of the nozzle. A plurality of angular passages are slanted away from the forward end of the nozzle, in the directions of arrows 74, the passages being identified by reference numerals 75. The nozzle has a grooved end 76 about which the end 72 of tube 70 is tightly resiliently disposed. The "head" of the nozzle 71 is recessed at 77, and the openings of passages 75, appearing as eyes, give the nozzle somewhat the appearance of the head of a snake. The rearward inclinations of the passages 75 cause the nozzle to be propelled through the colon by the water exiting therethrough, so that the nozzle and tube can be moved a considerable distance into the colon, as will be further explained.

On the other hand, nozzle 71b has the passages 75b angularly inclined toward the forward end of the nozzle, as shown. Similar parts of nozzle 71b are designated by the same reference numerals used in FIG. 5, with the suffix "b" added. This nozzle is designed with bends angled to allow proper and comfortable entry into the colon via the rectum. This structure affords the patient more comfort during the treatment, as nozzle 71b remains in this position throughout the treatment. Nozzle 71b is not propelled into the colon by water flow, and is usually inserted only about two inches into the colon via the rectum, the other end of the nozzle fitting being inserted about one inch into the end of resilient tube 70. The nozzle 71b remains stationary during treatment, and water is drawn further into the colon to soften dehydrated impacted matter for elimination by a vacuuming technique performed by the operator.

Referring to FIG. 4 of the drawings, the drawing shows schematically the form of the colon interior, in which lumps of feces 80 are disposed. The feces may be in lumpy form as shown, or may be a more or less congealed continuous expanse of fecal matter, fairly well compacted in the colon. When the nozzle 71a is introduced into the colon through the anus and sigmoid flexure, with water being delivered outwardly through the passages 75 with small force, the water impact with the feces in the colon and with the colon wall forces the streamlined forward end of the nozzle farther into the colon and at the same time tends to wash fecal matter which the water loosens toward the rectum. Therefore, the passage of nozzle 71a into the colon cleans the fecal matter from the colon and at the same time advances the nozzle farther into the colon by pulsating water flow. The nozzle may be passed into the colon past successive locations 71c–71g, and even farther, thereby cleaning virtually the full extent of the colon. The fecal matter 80a washed loose is propelled toward the rectum by the water flow both while the nozzle is advancing through the colon, and while the nozzle is being withdrawn from the colon by pulling on tube 70 outside of the body. The nozzle may be run repeatedly into the colon and withdrawn, to thoroughly wash the interior of the colon, if necessary.

Valve 54 may be of a type which will cause a pulsing water flow into the tube 70 and nozzle 71, water impulses such as are created causing very effective washing action similar to the teeth cleaning devices using pulsing water flow. Injection of oxygen or controlled breathing air into the water stream in tube 70 at valve 55 causes an increase in cleaning action of the water and tends to freshen the drainage from the colon. Of course, when oxygen is in use, care must be taken to avoid fires and explosions Injection of air has a similar effect, and is safer. The froth produced by oxygen or air injection has a high capability for dislodging solids from the bowel.

The apparatus is highly adaptable. Water may be fed to tube 70 in several manners, as described earlier.

Temperature of the water may be controlled by merely controlling the water mixture from sources H and C, or may be heated and controlled by means of heating coil 29, and temperature controller 30, or be further controlled by circulation of water from tank 20 through tank 28 with use of the heater coil 29.

Pressure of water delivered from tank 20 is, of course, dependent on the height of the water level in tank 20 above the nozzle, so long as the water is delivered by gravity.

When pump 57 is used, the pressure is not excessive, since pump 57 is selected to have a small delivery pressure and the pump discharge passes through pressure flow control valve 56. Pump 57 is used when more than gravity fed pressure is desired. To increase the pressure, control valve 56 may be adjusted to allow slightly more pressure and flow to the patient to acheive the desired results of removing impacted matter in the colon that will not break loose, at lower pressures and flows. The pump can also be used to pump agents such as barium into the colon for purposes of lower bowel examinations and X-Ray. When water is derived directly from sources H and C, the pressure at the nozzle is controlled by the pressure control valve 56.

Solenoid valve 54, previously mentioned, is controlled by an automatic intermittent timing relay device 54a, to cause the water flow to be pulsing, for enhanced washing action, also previosly mentioned.

It will be realized that treatment may be continued when electrical supply is interrupted by supplying water to the nozzle through conduit 46. Water may be supplied to the nozzles by any of the alternate routes mentioned earlier.

The water supplied to the nozzle should be warm, not hot or cold. If the water in the tank 20 is either too hot or too cold, the operator may drain some water from tank 20 and refill tank 20 with either cold or hot water from the H and/or C to adjust the temperature. The temperature indicator equipment 40–42 is a dual system, with two sensors and two indicators, as a safety precaution against the possibility that one system may not operate correctly.

A pair of control switches 83, 84 are mounted on the edge of cabinet top 11 within easy reach of the person supported on rest 15 and support 62. Switch 83 may be used by the patient to turn off solenoid operated valve 54, stopping water flow to patient, should the treatment become uncomfortable for some reason, or in case the patient feels a little ill, or in case the operator may have left the room and failed to return, or for other reason. Switch 84 may be used by the patient to turn off pump 57 when it is being used, for the same reasons. The presence of switches 83, 84 also has a beneficial effect on the outlook of the patient, as it gives the patient a sense of security to know that he or she has the ability to shut the apparatus down of his or her own volition.

A wash or flush water inlet is provided for the sight glass 68 in drain conduit 63. Conduit 85 having valve 86 leads from source, not shown, of water under pressure, there being a jet nozzle 87 adjacent the end of sight glass 68. When it is desired to flush out the interior of the sight glass, valve 86 is reopened, and a forceful spray of water is impinged against the sight glass interior. In this manner, the sight glass is kept clean so that it can fulfill its function of allowing viewing of materials passing therethrough. An additional wash conduit is provided for use in flushing down the basin 63a, at the interior of support 62. The conduit 88 has a flexible hose portion 89 to which is affixed a washing nozzle 90 movable by hand to direct a washing stream where desired, which can also be used in cleaning the basin or when necessary for washing matter from the skin of the patient. The wash liquid, of course, exits through drain 63.

As will be known to those skilled in the art, the treatments given through use of the described apparatus must be given with the water temperature at a warm but not hot temperature which is comfortable to the patient and is not damaging to tissues of the body. The water pressure, as emitted from the nozzle, should be sufficient to dislodge fecal matter from the colon, but must not be great enough to cause damage to tissues or to cause discomfort to the patient. The water volume must be sufficient to dislodge and wash out fecal matter at an efficient rate but not large enough to cause irritation or pressure which would be uncomfortable. Materials may be added to the water to improve washing action; for example, acetic acid in the form of cider vinegar may be added to the water to cause more rapid breakdown and removal of impacted feces.

During treatment, the patient should feel a gentle flow of warm liquid entering the lower bowel and in the beginning the patient may release at will. As the patient becomes accustomed to the gentle flow of the warm liquid, the operator may then ask the patient to hold a little longer while the operator applies compression to the ascending colon and/or the transverse colon. This procedure is used to create a vacuum to draw the warm liquid higher and further into the colon. A massage technique of the colon is used by the operator to help dissolve and break up impacted matter.

During the procedure, which last 30 to 50 minutes, the patient may choose to rest or be alone for a short period of 3. to 5 minutes. During the rest period, the flow of liquid would be off. Even though it is better practice, and the patient feels more secure, for the operator to be present continuously during the procedure, it is not absolutely necessary for the operator to be in the room at all times. The operator may even leave the room for a short period while the patient is receiving liquid. The patient may stop the flow of liquid to himself in the absence of the operator by use of the switches 83, 84, as has been described. If the water flow is not shut off by the switches 83, 84, then the patient may slide up on the backrest to remove the speculum (injection nozzle) from his rectum, in which case the water will just pass into the basin of support 62 and be drained away. The patient may do this whether or not the operator is in the room should he or she feel the need to do so.

If, after some period of treatment, the operator continues to feel hardness and large knots of impacted matter in the colon, and the patient is not defecating much, the operator may elect to introduce a gentle flow of oxygen or compressed air with the liquid by operation of valve 55. The introduction of oxygen serves to aerate the liquid to provide an effervescent and turbulent action. In the presence of such gases as methane and hydrogen sulfide, the introduction of oxygen creates, in addition to the effervescent and turbulent action, the urge to push thereby initiating peristalsis. The result is the original reason for providing the service of colonic irrigation, to aid in the removal of gases and impacted matter to provide for a better endoscopic or lower bowel examination, or generally to provide relief from constipation. Although the introduction of oxygen into the lower bowel may not have any therapeutic value, it does serve to achieve the desired result. It is evident from much observation that oxygen introduced into the lower bowel serves to help dissolve and break up impacted matter and helps to remove gases as well, as it is apparent that some of the oxygen is absorbed and tends to be refreshing and exhilarating. The only therapeutic value that it may have is that by introduction into the lower bowel, if there is any irritation in the colon, the oxygen will serve to speed up healing. In colonic irritation, the procedure of colonic irrigation itself serves to remove highly acid and toxic waste and contributes to better bowel movements and to hasten the healing process.

After 30 to 50 minutes of colonic irrigation, the patient should have eliminated enough waste to provide for good lower bowel examination by a doctor if such is to be performed. If the procedure was administered to relieve constipation, 30 to 50 minutes of colonic irrigation is usually sufficient. The apparatus must be thoroughly cleaned and disinfected following each use. Also, it is good practice to drain tank 20 and to fill it with water containing a germicidal cleaner, the latter then being drained and the tank thoroughly flushed with fresh water, so that not only the tank but all conduits therebelow are effectively cleansed. Tank 20 will not normally become contaminated, but it is better to clean equipment when not necessary than to take chances with patient health.

While preferred embodiments of the invention have been described and shown in the drawings, many modifications thereof may be made by a person skilled in the art without departing from the spirit of the invention, and it is intended to protect by Letters Patent all forms of the invention falling within the scope of the following claims.

I claim:

1. Apparatus for use in washing the colon of a person, comprising an elevated tank having a bottom outlet, means for filling said tank with water, said tank having an overflow drain at an upper level, a cross conduit having at one end a flow connection to an implement for delivering water into a person's colon, a solenoid operated shut-off valve and a check valve in series in said cross conduit, a manifold connected to said bottom outlet of said tank and having valve controlled first, second and third branches, said first branch being connected to said cross conduit between said check valve and said solenoid valve to permit flow of water from said tank to said cross conduit in by-pass relation to said solenoid operated valve, said second banch being connected to said cross conduit upstream of said check valve and said solenoid operated valve, and said third branch being connected to the inlet of a pump, the outlet of which is connected to said cross conduit at a point upstream of said check valve and said solenoid operated valve whereby water may be transmitted from said tank to said implement by gravity through said first and second branches or by said pump through said third branch.

2. The combination of claim 1, said means for filling said tank with water including water heater means.

3. The combination of claim 2, said water heater means comprising an elongate tank having an electric heating coil therein through which said water flows toward said tank, said water heater means also comprising a temperature controller for controlling operation of said heating coil in response to water temperature.

4. The combination of claim 3, said means for filling said tank with water comprising valved conduits from hot and cold water sources which are joined before entry into said water heater means, whereby water passed through said water heater means for delivery into said tank may be temperature controlled by controlling the proportion of hot and cold water from said sources and alternatively by operation of said heating coil and said controller.

5. The combination of claim 1, said tank having dual temperature indicating means whereby correct temperature of water therein is indicated in the event of failure of one temperature indicating means.

6. The combination of claim 5, wherein said means for filling said tank with water includes float valve means for controlling water flow into said tank and water level in said tank.

7. The combination of claim 1, wherein said means for filling said tank with water includes float valve means for controlling water flow into said tank and water level in said tank.

8. The combination of claim 1, said implement comprising a rectal nozzle.

9. The combination of claim 1, said implement comprising a nozzle having plural forwardly slanted angular water outlets.

10. The combination of claim 1, said implement comprising a nozzle having plural rearwardly slanted angular water outlets, whereby water discharge propels said nozzle further into the colon and tends to wash loosened feces toward the rectal outlet from the colon.

* * * * *